United States Patent [19]
Green

[11] Patent Number: 4,880,423
[45] Date of Patent: Nov. 14, 1989

[54] DISPOSABLE UNDERPANTS

[76] Inventor: Lyel A. Green, 5650 S. 2580 West, Roy, Utah 84067

[21] Appl. No.: 163,251

[22] Filed: Mar. 2, 1988

[51] Int. Cl.$^4$ .......................................... A41B 13/02
[52] U.S. Cl. .................................................. 604/391
[58] Field of Search ........................... 604/341, 385 A

[56] References Cited

U.S. PATENT DOCUMENTS

| | | | |
|---|---|---|---|
| 3,882,871 | 5/1975 | Taniguchi | 604/391 |
| 4,402,690 | 9/1983 | Redfern | 604/391 |
| 4,410,327 | 10/1983 | Baggoley | 604/391 |
| 4,617,022 | 10/1986 | Pigneul et al. | 604/391 |
| 4,680,030 | 7/1987 | Coates et al. | 604/391 |
| 4,681,581 | 7/1987 | Coates | 604/391 |
| 4,704,117 | 11/1987 | Mitchell | 604/391 |
| 4,773,906 | 9/1988 | Krushel | 604/391 |

Primary Examiner—C. Fred Rosenbaum
Attorney, Agent, or Firm—B. Deon Criddle

[57] ABSTRACT

A disposable undergarment for use by children and incontinent adults that may be placed and removed as a diaper and that, when assembled, can be moved up and down a user's body n the same manner as conventional brief-type undershorts.

1 Claim, 2 Drawing Sheets

DISPOSABLE UNDERPANTS

BRIEF DESCRIPTION OF THE INVENTION

1. Field of the Invention

This invention relates to easily installed and removed training pants for children and incontinent persons and is particularly concerned with providing disposable underpants that will provide for moisture collection and adequately secure retention of material therein while affording a protective outer waterproof covering.

2. Prior Art

The need for disposable clothing items for infants has long been recognized. Disposable diapers have become a very common item, used by many parents who do not want to have to wash reusable diapers or that find them inconvenient to use.

U.S. Pat. Nos. 3,424,162 and 4,205,679, both include a plastic outer layer and one or more absorbent inner layers. The underpants disclosed in these prior U.S. patents, may provide a practical solution to some of the problems encountered in handling human waste, but they do not solve all problems encountered. For example, the underpants shown by U.S. Pat. No. 3,424,162, appear to have a layered construction that would be difficult to produce and that would not, when assembled, provide for proper fitting around the legs and waist of an infant on which the training pants were placed. Also, the bindings at the edges of the underpants appear to be so constructed that they are likely to separate and come apart during use.

The underpants taught by U.S. Pat. No. 4,205,679, appear to require expensive machinery to form the required pleats and also appears that the pleating structure, itself, may very well cause moisture to follow the pleat patterns and to be discharged from leg openings rather than being retained by the underpants material itself.

The garments disclosed by the prior art patents are not intended to be assembled as a diaper and then to be used as training pants or as conventional underpants for incontinent persons.

OBJECTS OF THE INVENTION

Principal objects of the present invention provide low cost, underpants for use in training infants or the like, and for use by incontinent persons that will be durable enough to be repeatedly used, prior to such time as the underpants may be soiled, and to securely retain waste material to be disposed of along with the garment itself.

Other objects are to provide such a disposable underpants having puckered, elastized leg and waist openings and with an outer waterproof layer and plurality of inner absorbent layers all secured together at their periphery in such a manner as to make a very long lasting garment.

Still other objects are to provide a disposable underpants that is easily installed in the manner of a diaper and, after assembly, can be used as conventional underpants even by children and infirm persons and that will allow for ready removal as a diaper and entrapement of waste therein during disposal should the garment be soiled.

FEATURES OF THE INVENTION

Principal features of the invention include an outer waterproof layer, made of a thin, lightweight plastic material having absorbent batting bonded to an inside face thereof and a plurality of absorbent lining sheets, overlying the cotton batting and with the sheets and outer liner sewn together in a pattern to provide leg openings defined by leg bands and waist openings defined by waist bands and with the layers bound together with a bound stitch at sides and openings and elastized strip material in the waist and leg openings.

Strips of hooked and napped material, such as "Velcro" are provided to releasably secure the leg bands tightly around the legs of a user and to releasably secure the waist bands around the waist of a user.

Additional objects and features will become apparent from the following detailed description and claims.

THE DRAWINGS

In the drawings:

FIG. 1 is a perspective view showing the disposable undergarment of the invention assembled for use;

FIG. 2, an inside elevation view, laid flat and partially broken away; and

FIG. 3, an outside elevation view, laid flat.

DETAILED DESCRIPTION

Figure 1:
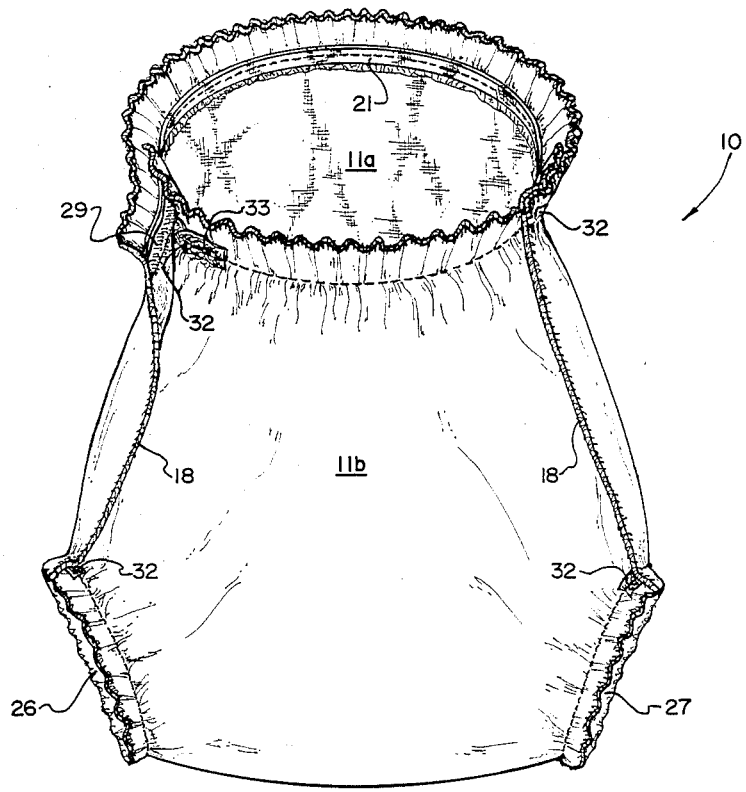
Figure 2:
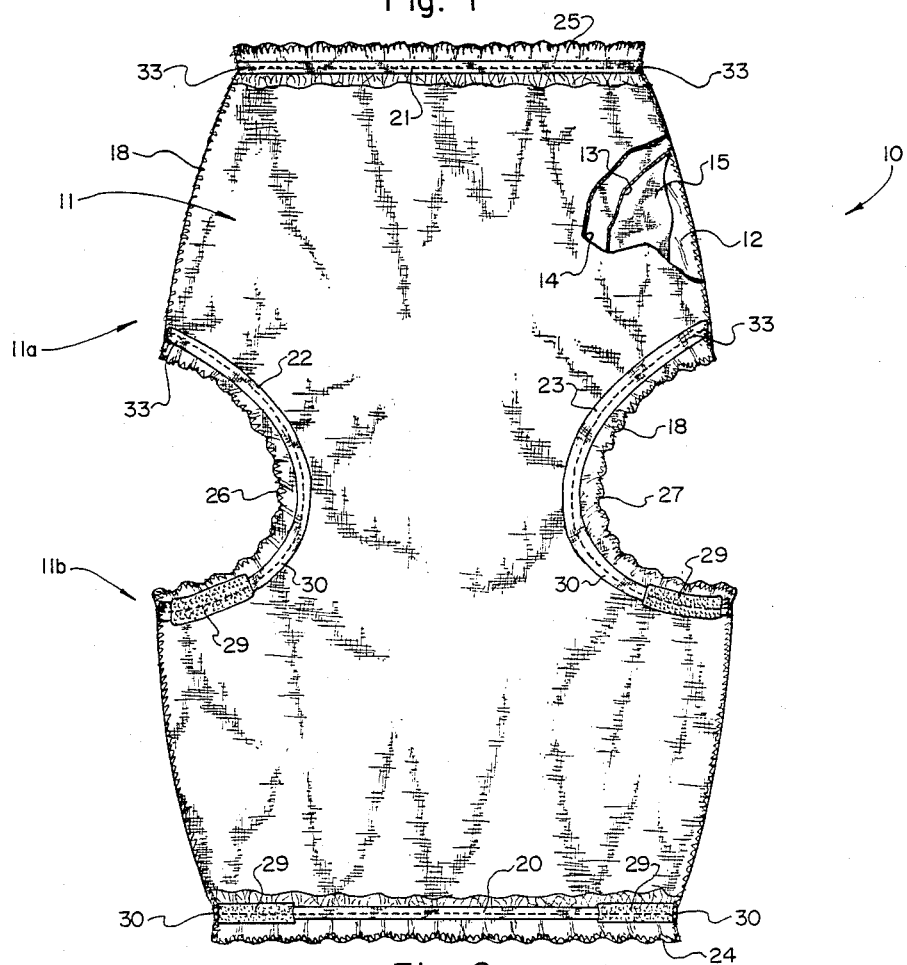

Referring now to the drawings:

In the illustrated preferred embodiment, the disposable underpants 10 of the invention comprises a sheet 11 of composite layers 12, 13, and 14. As best shown in FIG. 2, the sheet 11 comprises a backing 12 of waterproof material with gauze 15 on an inside face thereof; an absorbent tissue layer 13 overlying the gauze and a porous tissue layer 14 overlying the absorbent tissue layer.

The sheet 11 is cut into an hourglass configuration with a front portion 11a and a back portion 11b, the side edges are bound with a binding stitch 18.

Elastic strips 20, 21, 22 and 23 are stretched and sewn along a front edge 24 of portion 11a and a back edge 25 of back portion 11b and around leg openings 26 and 27, respectively. The elastic strips are placed on the absorbent tissue layer and are sewn to the sheet 11.

Strips of hooked material 28 (such as "Velcro") are sewn over the ends 29 of the elastic strips 20, 22 and 23 on the inside face of sheet 11 at the ends 30 thereof. Strips of napped material 32 that will be securely but releasably engaged by the strips of hooked material 28 are attached to the outside edge of sheet 11 and are sewn through sheet 11 to the ends 33 of the elastic strips 21, 22 and 23.

Underpants are formed by attaching the hooked material strips 29 on elastic strip 20 to the napped material strips 22 and the hooked strips 29 at ends 30 of elastic strips 22 and 23 to the napped strips 32 at the ends 33 of the elastic strips 22 and 23. By selective positioning of the hooked strips lengthwise relative to the napped strips the size of the undergarment can be varied, as desired. While the hooked and napped material strips provide a suitable adjustable, releasable attachment means, it will be apparent that other materials, such as reusable tapes could be used.

Figure 3:
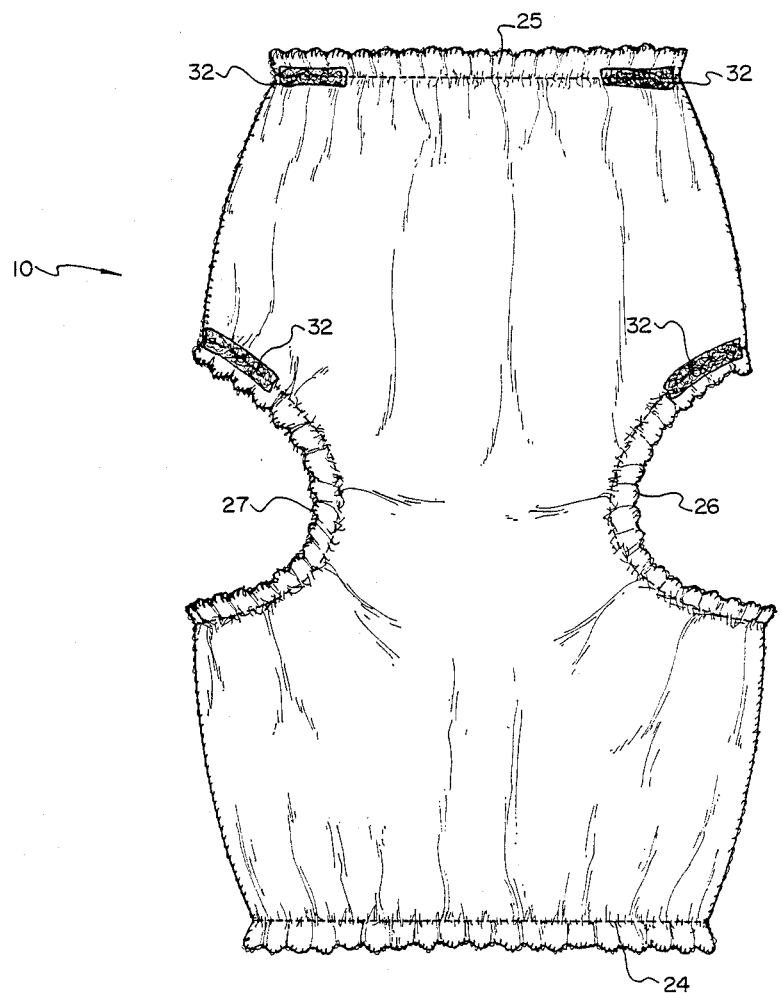

In use the underpants 10 of the invention can be packaged, stored and sold in the substantially flat condition of FIGS. 2 and 3; can be assembled for use as underpants as shown in FIG. 1; and can be folded to hold waste material by merely criss-crossing the interconnecting hooked and napped numbers.

Once the underpants have been formed the garment can be worn and used as conventional underpants. Thus, the elastic strips yield to allow the garment to be pulled down the user's body and to be pulled back up. However, should the garment be soiled it can be removed merely by releasing the releasable attachment means. The soiled garment can then be folded into a soil retaining condition, as previously described and the releasable attachment means can be reattached to hold the garment for disposal.

Although a preferred form of my invention has been herein disclosed, it is to be understood that the present disclosure is by way of example and that variations are possible without departing from the subject matter coming within the scope of the following claims, which subject matter I claim as my invention.

I claim:

1. A disposable underpants comprising
   a sheet of composite materials including a waterproof layer and at least one absorbent layer cut to an hourglass shape having a front portion with a front edge, a back portion with a back edge, a crotch portion between the front and back portions and leg openings at opposite sides thereof extending between side edges of the front portion and side edges of the back portion;
   strips of elastic sewn to the sheet along the front and back edges and along the leg openings;
   strips of hooked material sewn to and overlying ends of the elastic strips adjacent the leg openings at the front portion and to and overlying ends of the leastic at the front edge of the absorbent layer face of the sheet of compsite materials; and
   strips of napped material sewn through the sheet of composite material to and overlying opposite ends of the elastic means at the leg openings and to and overlying ends of the elastic strip at the back edge.

* * * * *